United States Patent [19]

Nochumson et al.

[11] Patent Number: 5,143,646
[45] Date of Patent: Sep. 1, 1992

[54] POLYSACCHARIDE RESOLVING GELS AND GEL SYSTEMS FOR STACKING ELECTROPHORESIS

[75] Inventors: Samuel Nochumson, Randolph, N.J.; Foner P. Curtis, Rockland, Me.; Jonathan H. Morgan, Camden, Me.; Francis H. Kirkpatrick, Owls Head, Me.

[73] Assignee: FMC Corporation, Philadelphia, Pa.

[21] Appl. No.: 691,041

[22] PCT Filed: Jan. 16, 1990

[86] PCT No.: PCT/US90/00184
§ 371 Date: Jun. 20, 1991
§ 102(e) Date: Jun. 20, 1991

[51] Int. Cl.$^5$ .................. B01J 13/00; C25D 13/00
[52] U.S. Cl. ........................ 252/315.3; 264/182.8; 264/299 R; 435/204; 436/806
[58] Field of Search .................. 435/22, 204; 436/806; 204/182.8, 299 R; 252/315.3

[56] References Cited

U.S. PATENT DOCUMENTS

| | | | |
|---|---|---|---|
| 3,507,851 | 4/1970 | Ghetie et al. | 260/209 |
| 3,956,273 | 5/1976 | Guiseley | 204/180 G |
| 4,275,196 | 6/1981 | Shainoff | 536/115 |
| 4,290,911 | 9/1981 | Cook et al. | 252/316 |
| 4,312,727 | 1/1982 | Shainoff | 204/180 G |
| 4,312,739 | 1/1982 | Hansson | 204/299 R |
| 4,319,975 | 3/1982 | Cook | 204/180 G |
| 4,559,120 | 12/1985 | Royse et al. | 204/182.8 |
| 4,695,548 | 9/1987 | Cantor et al. | 435/179 |
| 4,774,093 | 9/1988 | Provonchee et al. | 424/493 |
| 4,948,480 | 9/1990 | Christy, Jr. et al. | 204/182.8 |
| 4,983,268 | 1/1991 | Kirkpatrick et al. | 204/182.8 |
| 5,019,232 | 5/1991 | Wilson et al. | 204/182.8 |
| 5,066,376 | 11/1991 | Osterhoudt et al. | 204/182.8 |
| 5,069,773 | 12/1991 | Frangioni | 204/299 R |
| 5,073,603 | 12/1991 | Ponticello | 525/350 |

OTHER PUBLICATIONS

H. J. Bode, "The Use of Liquid Polyacrylamide in Electrophoresis" (1977) Analytical Biochemistry 83, 204–210.

M. Dumais and S. Nochumson, "Small DNA Fragment Separation and M13 Cloning Directly in Remelted Nu-Sieve GTG Agarose Gels" Biotechniques vol. 5, No. 1 (1987).

Saiki, et al., "Primer-Directed Enzymatic Amplification of DNA with a Thermostable DNA Polymerase" Science, 239:486–491 (1988).

S. Nochumson "Seaprep 15/45: A New Agarose with Low Gelling and Remelting Properties for Preparative Electrophoresis" Electrophoresis '81 Allen, Arnaud (Eds.) W. deGruyter & Co. Pub. New York (1981).

Perlman, Chikarmane, Halvorson "Improved Resolution of DNA Fragments in Polysaccharide-Supplemented Agarose Gels" Analytical Biochemistry 163:247–254 (1987).

"Advances in Carbohydrate Chemistry and Biochemistry" Academic Press, New York (1975) Vol 31 p. 203, et seq.

Reich & Stivala "Elements of Polymer Degradation" McGraw Hill Book Co. New York (1971).

Laemmli "Cleavage of Structural Proteins during the Assembly of the Head Head of Bacteriophage T4" Nature Vol. 227:680–685 (1970).

Hames & Rickwood "Gel Electrophoresis of Proteins: A Practical Approach" IRL Press (pub) (1981) 7–17.

Ornstein "Disc Electrophoresis—I, Background and Theory" Annals of the NY Academy of Sciences Vol. 121:321–349 (1964).

Davis "Disc Electrophoresis—II, Method and Application to Human Serum Proteins" Annals of the NY Academy of Sciences Vol. 121:404–427 (1964).

Jovin, et al. "Multiphasis Buffer Systems Output" U.S. Government Printing Office NTIS no. 196085–196092, 203016 (1970) Out of Print.

Jovin "Multiphasic Zone Electrophoresis" Biochemistry Vol. 12:871–898 (1973).

Primary Examiner—Richard D. Lovering
Assistant Examiner—N. Bhat
Attorney, Agent, or Firm—Mark A. Greenfield; Robert L. Andersen

[57] ABSTRACT

Electrophoretic resolving gel compositions, discontinuous stacking gel systems containing these and other resolving gel compositions, and kits for preparing such gel systems, comprising one or more polysaccharide hydrogels of which agarose is typical wherein at least one of the gels in the resolving gel composition has been derivatized and at least one of the gels in the resolving gel composition has been depolymerized sufficiently to reduce its casting-effective viscosity.

33 Claims, No Drawings

POLYSACCHARIDE RESOLVING GELS AND GEL SYSTEMS FOR STACKING ELECTROPHORESIS

This invention relates to electrophoretic gels. More particularly, the invention relates to electrophoretic resolving gels having improved sieving and working properties comprising one or more polysaccharides or polysaccharide derivatives, at least one of which has been partially depolymerized; electrophoretically effective discontinuous gel system combinations of resolving gels with one or more polysaccharide or derivatized polysaccharide stacking gels; and kits comprising the gel system ingredients in premeasured or hydrogel form.

Crosslinked polyacrylamide, produced by polymerizing acrylamide containing a few percent of N,N'-methylenebisacrylamide, is extensively employed as the matrix for gel electrophoresis. This is due primarily to three properties of the polymer, namely: excellent mechanical strength, adherence to glass surfaces and wide control of pore size, thereby permitting fractionation of moieties ranging from simple amino acids to complex biological substances having molecular weights in the millions.

There are, however, certain attributes of cross linked polyacrylamide which detracts from its application as an electrophoretic medium. A major concern is that the gel is formed by a polymerization reaction utilizing free radicals, which is exothermic. As is well recognized, free radical reactions depend on a variety of parameters such as concentration of initiators which themselves tend toward instability, monomer purity, temperature, time, oxygen tension and absence of other inhibitors; managing these factors can require an inordinate amount of care and attention in order to achieve reproducible results. Another at least potential objection to crosslinked polyacrylamide is the possible health hazard from handling of the precursor monomers, acrylamide having been found to be a neurotoxin.

Over the past several years, a great deal of effort has been expended in the investigation and development of electrophoretic gel systems which are free of the problems associated with polyacrylamide. As a result of these research efforts, the polysaccharide agarose has emerged as a gel candidate showing considerable promise. Agarose is non-toxic, has high gel strength, low electroendosmosis and does not require free radical polymerization for gel formation. Agarose is a naturally occurring, substantially linear polymer which forms gels that are thermally reversible, thereby enabling separated components to be recovered from the melted gel.

Gels prepared with native (non-derivatized) agarose exhibit a characteristic coarse pore structure, a feature which renders them the preferred medium for the electrophoretic separation of large macromolecules. Generally speaking, primarily proteins having molecular weights in excess of about 500,000 (500 kD) can be resolved. Although smaller molecular weight entities can be resolved (restricted) by increasing the agarose content of the gel, this produces high viscosities in the agarose casting solutions, which make them very difficult to handle. Agarose gels are thus precluded from being used in a number of analytical and preparative procedures.

The large pore limitation of agarose gels can be diminished and their sieving action improved by forming the gels from certain agarose derivatives having a finer pore structure than the parent agarose. One preferred class of such modified agarose is hydroxyalkylated agarose produced by replacing 1 to 4 hydroxyl hydrogen atoms in the agarobiose units of the agarose polymer chain with hydroxyalkyl moieties. An especially preferred member is hydroxyethylated agarose obtained by reacting agarose with 2-chloroethanol in the presence of alkali. Gels from hydroxyethylated agarose are capable of resolving proteins of from about 50 kD to about 600 kD. Moreover, such gels have lower melting points than native agarose gels, an advantage when recovering sensitive biological substances from the remelted gels.

Hydroxyethylated agarose is sold by FMC Corporation, BioProducts Group, Rockland, Me. 04841 U.S.A. under the trademark SeaPlaque®. Further details on the description and preparation of hydroxyalkylated agarose will be found in U.S. Pat. No. 3,956,273—Guiseley, which is incorporated herein by reference.

Although a decided advance in the art, the hydroxyalkylated agaroses, as with native agarose, form casting solutions whose viscosity increases with gel concentration. This makes it difficult to prepare gels of sufficient concentration to achieve maximum sieving action.

It has been reported that the sieving properties of agarose gels can be improved by combining them with other gel forming materials such as polyacrylamide; see Bode, H. J. (1977) Anal. Biochem. 83, 204–210. However, such mixtures have compatibility problems, especially when they contain high percentages of agarose. Moreover, such heterogeneous agarose blends have not afforded consistent improvement of the protein separation patterns. This is especially true when conducting submerged electrophoresis, where additives not incorporated in the gel structure have a tendency to diffuse out of the gel unless incorporated in the buffer as well. In contrast, an all agarose system forms an integrated gel.

While various agarose sieving gels are known, all sieving gels are not optimum for use as resolving gels. Examples of known sieving gels include the following.

NuSieve® GTG is an agarose sieving gel, which is a product of FMC Corporation, BioProducts Group, Rockland, Me. 04841, U.S.A., whose use has been described in "Small DNA Fragment Separation and M13 Cloning Directly in Remelted NuSieve® GTG Agarose Gels" by Dumais & Nochumson, *BioTechniques,* 5:62 (1987). Buffer systems disclosed in FMC Corporation literature as commonly used with NuSieve GTG agarose include:

TAE (40 mM Tris, 20 mM acetate, 2 mM EDTA at pH 8.0) and

TBE (89 mM Tris, 89 mM borate, 2 mM EDTA at pH 8.0).

NuSieve comprises a native agarose which has first been derivatized to hydroxyethyl agarose and has then been partially depolymerized.

Another known sieving agarose is a combination of one part SeaKem® native agarose (a product of FMC Corporation, BioProducts Group, Rockland, Me. 04841 U.S.A.) with three parts of the above described NuSieve® agarose. This combination has been disclosed as useful in Polymerized Chain Reaction (PCR) procedures by Saiki, Gelfand, Stoffel, et al., in "Primer-Directed Enzymatic Amplification of DNA with a Thermostable DNA Polymerase", *Science,* 239:486–491 (1988).

Still another known sieving gel is SeaPrep ® hydroxyethyl (derivatized) agarose, a product of FMC Corporation, BioProducts Group, Rockland, Me. 04841 U.S.A. There is a disclosure of the use of this product for sieving in electrophoresis by Nochumson, S. in *Electrophoresis* '81, 213-218, Allen & Arnaud (eds.), W. de Gruyter & Co. (pub.), New York (1981).

Other known sieving gel compositions include the mixture of agarose with hydroxyethyl cellulose as disclosed by Perlman, Chikarmane, and Halvorson in "Improved Resolution of DNA Fragments in Polysaccharide-Supplemented Agarose Gels", *Analytical Biochemistry*, 163:247-254 (1987).

This invention affords [1] novel polysaccharide resolving gel compositions; [2] novel "gel systems" comprising the foregoing novel and/or known polysaccharide resolving gel compositions electrophoretically associated with discontinuous polysaccharide stacking gels; and [3] kits comprising combinations of premeasured dry powder and/or premixed hydrogel resolving gels and discontinuous stacking gels, all of the foregoing optionally containing appropriate buffer systems. The resolving gels of this invention are particularly characterized by being capable of forming gels with improved sieving and resolving properties which can be prepared in high concentrations and without the handling problems normally presented by increasingly viscous casting solutions. Resolving gels and resolving-stacking gel systems have known utility in gel electrophoresis.

Other than in the operating examples, or where otherwise indicated, all numbers expressing quantities of ingredients, parameters, or reaction conditions used herein are to be understood as modified in all instances by the term "about".

As used herein the term "discontinuous" refers to a differential between a resolving gel and an associated stacking gel as to at least one of: gel pore size or polymer composition or the respective associated buffers' ionic strength, ionic composition, or pH. It is such a differential (discontinuity) that permits the stacking gel system of this invention to operate in the manner described herein. As is known in the electrophoresis art, there usually must be a second discontinuity between the electrode buffer and the buffer of the gel used. This second discontinuity is not part of this invention and is not included within the term "discontinuous" except where otherwise stated.

As used herein, the term "polysaccharide" refers to a native or derivatized thermoreversible and/or pH-reversible hydrogel-forming polysaccharide preferably selected from among: agar, agarose, curdlan, gellan, konjac, pectin, pullulan, and to a lesser degree alginate and carrageenan, and the like; as well as thermoreversible or pH-reversible hydrogel combinations of any of the foregoing with either another polysaccharide or a non-polysaccharide polymer which associates firmly with the gel-forming polymers so that it does not significantly dissociate under electrophoretic conditions. (Linear polyacrylamide does not associate firmly with the gel-forming polymers of this invention.)

In contrast to the present invention, the polyacrylamide gels of the prior art are known as neither pH- nor thermo-reversible. The hydrogel compositions and gel systems of the present invention specifically exclude acrylamide and do not require cross-linking or polymerizing agents.

The gels of this invention can be used in vertical, horizontal, and inverted casting formats using standard equipment and buffers, and it is the increased ease of such casting without sacrifice of gel strength or resolving power that constitutes a most important advantage of this invention. Because they are thermoreversible and/or pH-reversible, the resolving and (separated) stacking gels of the present invention can be remelted after electrophoresis, enabling quick sample recovery and possible gel recovery and further gel utilization.

[I] In a first embodiment this invention affords a resolving gel composition comprising, preferably consisting essentially of, one or more (preferably two or more, more preferably two) polysaccharide hydrogels, at least one of which has been derivatized, and independently, at least one of which has been partially depolymerized sufficiently to reduce its viscosity to a degree that the casting ability of the resolving gel is improved, but not to the point where the resolving gel's strength is weakened beyond that required in electrophoretic procedures. It is possible to use as the hydrogels a mixture of a given derivatized hydrogel and the same gel after depolymerization. This may otherwise be stated as "depolymerized sufficiently to reduce the casting-effective viscosity of the resolving gel". The gel component polymers (when more than one is present) are physically blended (mixed) prior to formation of the hydrogel, and where the same polymer has been both depolymerized and derivatized, the order of such depolymerization and derivatization is not important. The inventive resolving gel preferably also comprises a suitable electrophoretic buffer, as will be discussed below.

The preferred polysaccharide for use in preparing the resolving gel composition of this invention is an agarose, and further disclosure herein will be stated in terms of agarose, although one or more of the other mentioned polysaccharides may be substituted therefore in a manner known in the art. Preferred agaroses for preparing the resolving gel composition are any native or derivatized agarose, examples of which include one or more of: native agarose; hydroxyalkylated agarose (more preferably hydroxy-$C_{2-4}$-alkoxylated agarose, most preferably hydroxyethyl agarose); and dihydroxyalkylated agarose (more preferably dihydroxypropyl agarose, most preferably 1,2-dihydroxypropyl agarose), at least one of which has been depolymerized to reduce its viscosity at least to a casting-effective degree.

The most preferred 1,2-dihydroxypropyl agarose component of the inventive resolving gel composition is a known material which is prepared by reacting agarose with glycidol under alkaline conditions. It is isolated as a white powder or granules which form low melting gels with water. For a detailed description of its preparation, reference is made to U.S. Pat. No. 4,312,727—Shainoff.

In so far as this invention is a resolving gel composition per se, it should be noted that it excludes: (i) a single hydroxyethyl agarose hydrogel which has been subsequently partially depolymerized by gamma irradiation, [previously disclosed as useful for other purposes] and (ii) a mixture of three parts of (i) with one part of native agarose, [previously disclosed as useful for Polymerized Chain Reactions (PCR's)].

It is a critical aspect of the resolving gel compositions of this invention that they contain at least one agarose which has been depolymerized (i.e. degraded) sufficiently to reduce its viscosity. It is preferred that the viscosity of at least one agarose of the resolving gel composition is depolymerized until its viscosity is reduced to 5–40 cps (mPa's) when measured at 75° C. in a 3%/volume aqueous solution.

In the broadest aspect of this invention, the method of depolymerization is not critical, and is limited only in that it must achieve sufficient depolymerization to reduce the viscosity of the entire resolving gel or preferably one of the two or more resolving gel polysaccharide components to 5–40, preferably about 30–40 cps when measured in a 3% aqueous solution at 75° C. A centipoise (cps) is approximately equal to a milliPascal (mPa's). It is particularly important, however, that the method of depolymerization does not introduce contaminant ions and that it does not change the integrity of the polymer.

Techniques for the depolymerization (degradation) of polymers are known in the art and any suitable method may be used including: exposure to gamma radiation; exposure to radiation other than gamma such as actinic; acid hydrolysis, including "Smith Degradation" involving reduction of periodate-oxidized polysaccharide with borohydride, followed by mild hydrolysis with acid [see "Advances in Carbohydrate Chemistry and Biochemistry", Academic Press, New York, 1975, volume 31 page 203, et seq.]; alkaline hydrolysis; catalytic hydrolysis, for example by using iron EDTA (ethylenediaminetetraacetic acid) or NTA (nitrilotriacetic acid) with or without a transition metal addition; enzyme hydrolysis; mechanical shearing; thermal depolymerization such as by extended heating at 80°–120° C. in a dry or wet (aqueous solution) state; or other known means. Many known techniques and aspects of polymer degradation useful in this invention are described in "Elements of Polymer Degradation", by Reich and Stivala, McGraw Hill Book Co., New York, 1971, to which reference may be made.

Preferred methods of depolymerization are irradiation by exposing the polysaccharide to a source of gamma radiation, usually Cobalt 60, (at a dosage of 200 mR to 800 mR for agarose); acid hydrolysis such as "Smith Degradation" under controlled conditions; and thermal degradation.

Some loss of sieving efficiency is incurred by the depolymerized (degraded) resolving gel component but this is compensated in a preferred aspect by the presence of a non-depolymerized component in the resolving gel blend. Thus, there is a trade-off in which some sieving action is sacrificed for reduced viscosity in order to arrive at a component mix that results in manageable gel casting solutions.

In general, the extent and intensity of the depolymerization treatment is that which is sufficient to depolymerize at least one agarose polymer to the point whereby either taken alone or combined with other agaroses it provides workable casting solutions for the resolving gel, that is, so that its viscosity is reduced at least in a casting-effective amount. Desirably, the aqueous casting solution for forming the resolving gel has a viscosity of 20 to 450 cps and the total amount of the one or more agaroses in the resolving gel is 2 to 12 wt %, preferably 4 to 8 wt %. Where two agarose ingredients (a) and (b) are present in the resolving gel, the weight ratio a:b is 1:0.11–9, preferably 1:1.

In preparing the inventive resolving gels the individual gel forming polysaccharide components can be combined in the dry state and hydrogels prepared from the mixture; alternately, each component can be dissolved to give separate solutions which are mixed and then cast into composite gels. Desirably, the degree of derivatization and to a lesser extent the concentration of the polysaccharide (when agarose) components is such that gelling temperatures (Tg) are 10°–25° C. A Tg below about 10° C. gives rise to weak or fragile gels which tend to crack whereas a Tg above about 25° C. falls off in sieving capacity.

Total concentration of the polysaccharide (preferably agarose) components in the resolving gel also may be defined by the viscosity of the casting solutions, which, if above about 1500 cps at 75° C., makes gel casting difficult or impractical. The viscosity also will depend on the type and proportion of each component. For instance, where a blend contains predominately a depolymerized agarose such as gamma irradiated hydroxyethylated agarose, a gel containing 20% of the blended agaroses could be cast. The inventive resolving gel compositions can be formed into an electrophoretic hydrogel medium for the separation of a wide selection of biological macromolecules, particularly including sodium dodecyl sulfate (SDS) protein complexes, in molecular weight ranges of 0.5 to 10,000, preferably 3 to 570, most preferably 10 to 200, kD (kiloDaltons).

Buffers known in the art as useful in electrophoresis are utilized in connection with the resolving gels of this invention. For a further discussion of suitable buffers, see the below disclosure related to the inventive gel system embodiment. A borate-containing buffer system is preferred when agarose is the polysaccharide, since the preponderance of hydroxyl moieties in the one or more agaroses are available for borate-complexing. As is known in the art, this can act as a crosslinking mechanism to further reduce the pore size of the agarose gel system for improved resolution of the protein molecules during electrophoresis. It has now been discovered that by adding the hydroxy moieties in a 1,2-dihydroxy agarose, cross-linking is potentiated by further addition of a borate.

It has also been found that adding at least one low molecular weight polyol to the resolving gel composition may increase its capacity for resolving smaller molecular weight protein substances, particularly those up to 20 kD. Additionally, polyols (particularly glycols) may increase the optical clarity of the resolving gel composition. These findings constitute an optional further aspect of the invention. Polyols useful herein must be water soluble and must not come out of solution at the temperatures at which the inventive compositions are prepared or utilized, especially at ambient room temperatures. The polyols preferably have molecular weights in the range 60–2,000, more preferably 60–600. Exemplary polyols include ethylene glycol, glycerol, sucrose, sorbitol and polyoxyethylene glycols of 200 to 600 D. The polyols, when present, are at concentrations of 1 to 5, preferably 5, % w/w based upon the resolving gel.

[II] In a second embodiment, this invention affords a gel system which comprises the combination of the novel and or certain other resolving gel compositions of this invention with stacking gels, in a protein electrophoresis system which utilizes the discontinuous-buffer concept, as exemplified in Laemmli, but as a critical distinction, is an entirely or substantially polysaccharide (preferably agarose) system, rather than polyacrylamide [see Laemmli, U. K. "Nature" 227:680–685 (1970)]. The gel systems of this invention afford (1) separation of proteins in the molecular weight range of 10,000 to 200,000 daltons with excellent resolution of individual protein bands; (2) compatibility with existing protein electrophoresis equipment and protein detection techniques; (3) moderate viscosity for easy handling; (4) melting of the gels at low temperature for easy sample recovery; and (5) avoidance of the toxic ingredients used in polyacrylamide gels.

In one preferred embodiment, a gel system as disclosed herein may comprise as the resolving gel a blend of (A) hydroxy-$C_{2-4}$-alkylated agarose and (B) 1,2-dihydroxypropyl agarose, at least one of which agarose components, preferably the hydroxyalklated agarose, has been depolymerized, preferably by acid hydrolysis or gamma radiation, more preferably the latter.

The resolving gel composition of this invention (having relatively small pores) may be combined with a superposed or adjacent stacking gel (having relatively large pores), the combination forming a "gel system" which is another embodiment of this invention. Techniques for forming and utilizing resolving gels in combination with stacking gels are known in the art. Biological materials to be separated are suspended in an appropriate buffer and applied to wells in a large(er) pore stacking gel which is superposed upon a small(er) pore resolving gel within an electrophoresis apparatus. The ionic composition and pH of the stacking gel are such that the ions migrating into the gel (i.e. "trailing" ions) from the electrode buffer (i.e. "running" buffer), have a lower mobility than the sample molecules or stacking gel (i.e. "leading") ions. The sample is gradually compressed (i.e. stacked) during the movement of the sample "front" through the stacking gel by the position of the sample front between the leading and trailing ion fronts. At the interface of the stacking and resolving gels, conditions change—usually one (or preferably more) of the buffer ionic strength and pH and the gel pore size—to permit the trailing front to accelerate and move ahead of the sample molecules (which then "unstack"). The sample becomes compressed into a very thin zone, so that the entire sample enters the resolving gel at about the same time and as a result, when the sample is separated by molecular weight during electrophoresis in the resolving gel, the different species in the sample are resolved as sharp bands.

In addition to Laemmli, supra, a good explanation of stacking gels will be found in "Gel Electrophoresis of Proteins", Hames, B. D. & Rickwood, D. (ed.), IRL Press, Washington, D.C. (1981) at pages 7 through 17. Other descriptions of stacking gel technology and theory will be found in Ornstein, L. "Disc Electrophoresis—I Background and Theory", Annals N. Y. Acad of Sciences, 121:321-349 (1964); Davis, B. "Disc Electrophoresis—II Method and Application to Human Serum Proteins", Annals N.Y. Acad. Sciences, 121:404-427 (1964); Jovin, T., et al., "Multiphasic Buffer Systems Output", U.S. Government Printing Office NTIS no. 196085- 196092 and 203016 (1970); and Jovin, T. "Multiphasic Zone Electrophoresis", Biochemistry, 12:871-898 (1973).

The resolving gel buffer and stacking gel buffer may be the same or different, depending upon whether a buffer differential is desired as the sole or a partial source of the discontinuity that must exist between the resolving and stacking gels within the inventive gel system. Any buffer that is known to be useful within a stacking gel system is useful herein, and an extensive (but incomplete) listing of such buffers will be found in Jovin, Dante, & Chrambach, "A Multiphasic Buffer Systems Output", U.S. Government Printing Office, NTIS No. 196085 - 196092, 203016 (1970), which listing is incorporated herein by reference.

Preferred buffers are Tris-borate for the resolving gel and Tris-HCl for the stacking gel, with Tris-glycine used for the electrode buffer. However, any biocompatible buffer or buffers will work for the three foregoing. The same buffer may be used for the electrode buffer and the resolving gel buffer where the (interposed) stacking gel buffer is discontinuous. A single buffer can also be used for adjacent gels, if their is another basis for the required discontinuity within the gel system, such as pore size. Where the same buffer is used, it can be varied as to ionic strength (i.e. concentration) to create the required discontinuity. The pH can be varied using the same buffer, which itself may be an adequate discontinuity for the purposes of the subject invention. Sodium phosphate buffers as disclosed by Weber and Osborn may be used as may other amines substituted for Tris such as triethanolamine, triethylamine, and the like. Other suitable buffers are histidine, imidazole, and lysine. If the anion is a buffer, then the cation need not buffer and can be an alkali metal or a quaternary amine. Ammonia is usable but is not preferred because of volatility. Divalent cations are not preferred because of possible interactions with the samples being separated.

Anions are often non-buffering when used with buffering cations. Examples are sulfate, chloride, acetate, (often non-buffering, as when at pH 8), and the like. Buffering anions can also be used. Examples are phosphates, citrate, and carbonate/bicarbonate. Monovalently charged anions are usually preferred.

Zwitterions are of use, especially in the stacking gel, where they are strongly preferred. Glycine in particular may be used as the trailing ion. "Good's Buffers" such as HEPES are often zwitterions, and can be used either for the stacking gel or for other parts of the gel system, depending on the pH. It may be noted that the classical Kolrausch stacking depends on the trailing ion—often, but not always, a zwitterion— going from a low mobility state above the boundry to a high mobility state beyond the boundry. Kolrausch stacking is included within the present invention which, however, is expanded conceptually well beyond the Kolrausch concepts. Glycine (aminoacetic acid) is fully zwitterionic at pH 6.8, about halfway between the two pk's, and thus has low mobility. At pH 8, below the boundry, the amine is partially deprotonated, and thus the mobility of the glycine is sharply increased. For example, MOPS (3-N morpholino ethanesulfonic acid) has a sulfonic acid and a tertiary amine, and will increase in mobility on going through its amine pk at pH 7.2. Design of systems using these compounds is well known, as illustrated in Jovan, Dante & Chrambach (1970), supra.

It is to be understood that the electrode buffer utilized in electrophoresis procedures with the inventive resolving gels, gel systems and kits may be any of those already known in the art and does not form a part of this invention. Such electrode buffers may themselves be discontinuous from the stacking gel buffer as to ionic strength or composition or pH, according to Kolrausch, but do not have to be.

The stacking gel itself is at least one of the previously identified polysaccharides, agarose or derivatized agarose being preferred. It should have a high gel strength and an electroendosmosis [EEO] value between low negative and slightly positive. Particularly useful is a gel system wherein the EEO value has an $m_r$ of from $(-)$ 0.15 to $(+)$ 0.05, preferably $(-)$ 0.10 to $(+)$ 0.05, more preferably (−) 0.03 to (+) 0.03, most preferably approaching zero, (such as ±0.01.

Useful materials for the stacking gels according to this invention include any polysaccharide as defined herein. Particularly useful are agarose or derivatized agarose gels commercially or otherwise available which have a low EEO or are neutral or even slightly positive, such as those already known as useful for isoelectric focusing, preferably those also having a high gelling temperature. Such gels include DEAE [diethylaminoethyl]-agarose [i.e. treated with CED (chloroethyldiethylamine)]; EDAC [1-ethyl-3(3-dimethylaminopropyl) carbodiimide hydrochloride]-treated ion-exchanged agarose; and agarose gels such as disclosed in U.S. Pat. Nos. 4,312,739 and 4,319,975 both of which are incorporated herein by reference.

Thus, a 6% solution of the agarose blend in a borate-containing buffer system is typically cast as a vertical gel, using a 1% stacking gel having a zero to slightly positive electroendosmosis, for concentrating the protein sample mixtures.

After gellation of the agarose solutions, the gel medium is used in carrying out electrophoretic separations and then processed in the usual manner. The techniques for using resolving gels in combination with stacking gels for electrophoretic separations are generally well known and, therefore, a detailed description need not be recited herein. The resulting protein separation patterns are comparable to those obtained in crosslinked polyacrylamide gels.

[III] In a third embodiment, this invention comprises a kit containing: [1] a prebuffered resolving hydrogel or gel solution or premeasured gel powder with buffer; and [2] a prebuffered stacking hydrogel or gel solution or premeasured gel powder with buffer (optionally with a color indicator present in an indicator-effective amount, especially in the stacking gel and optionally with one or more polyols as disclosed above), especially in the resolving gel); each in separate containers. Typically, the resolving gel aqueous solution consists essentially of 6% agarose inventive resolving gel composition in Tris-borate buffer at a pH of 8.5 and the stacking gel aqueous solution consists essentially of 1.5% agarose stacking gel composition in Tris-HCl buffer at a pH of 6.8, together with 5 um/ml of phenol red color indicator. The inventive gel system is then prepared by heating each solution and pouring it sequentially into a pre-warmed cassette to form two layers. As a still further embodiment, the inventive kit may comprise stacking gel spacers of various thicknesses, typically 0.75 mm, 1.0 mm, and 1.5 mm; as well as other physical accessories. These spacers are used in gel casting to create a smooth interface between the stacking gel and the resolving gel, in known manner. The kit may also contain, in a separate container, prepared electrode or sample buffers, and the like. The combined gel composition, cast using the kit as described above, affords excellent separation of SDS-treated proteins in the range of 10k-200 kD MW.

EXAMPLE 1

Preparation of an Agarose Stacking Gel System

A. Resolving gel:

A two component, entirely agarose, small pore resolving gel was prepared. Component 1 was prepared by exposing powdered hydroxyalkylated agarose (SeaPlaque®, a product of FMC BioProducts, Rockland, Me. 04841, U.S.A.) to gamma irradiation at a 600 mR dosage which reduced the viscosity of a 4% aqueous solution to 30 cps to 40 cps at 75° C. Component 2 was the 1,2-dihydroxypropyl derivative of agarose (glycerated agarose) as described in Example 1 of U.S. Pat. No. 4,312,727.

Both Components 1 and 2 were blended at a 50/50 (w/w) ratio and six (6) grams were dissolved in 94 mL of a buffer containing 0.5M Tris and 0.16M boric acid, adjusted to pH 8.5 with HCl. The viscosity of the resulting solution at 75° C. was within 400–450 cps. In addition, the resulting agarose blend had both low gelling (24°-28° C.) and remelting (65° C.) temperatures enabling manageable gel casting and preparative procedures for protein recovery.

B. stacking gel

A large pore agarose stacking gel was made from the diethylaminoethylagarose derivative described in Example 1 of U.S. Pat. No. 3,507,851, which is prepared by reacting agarose with 1-chloro 2-diethylaminoethane in the presence of sodium hydroxide. A 1% solution was prepared by dissolving 1 gram of this agarose derivative in approximately 100 mL. of 0.25M Tris-HCl buffer pH 8.8. The resulting stacking gel allowed the applied proteins to concentrate into a narrow band before entering the small-pore agarose resolving gel.

EXAMPLE 2

Electrophoresis of Standard Protein Markers and *E. coli* Proteins

Liquefying The Gels: Separate flexible bottles containing the small pore agarose resolving gel and the large pore stacking gel, as respectively described in Example 1, were placed in a 95° C. water bath for 5-10 minutes to liquefy their contents. Each bottle was swirled before casting.

Cassette Assembly: A vertical casting cassette was assembled in the following manner. One mL deionized distilled water was applied to the glass backing plate (140 mm×160 mm) of a casting cassette. A piece of plastic support film having one hydrophilic side (Gel-Bond ® a product of FMC Corporation, BioProducts Group, Rockland, Me. 04841, U.S.A.), was placed atop and smoothed down using a rubber roller. Two side spacers 140 mm×10 mm×1 mm, were then placed on the GelBond ® film. A notched top plate was placed on top of the spacers and the cassette was clamped around its edges with 1" stationary clamps. A stacking spacer (140 mm×35×mm×1 mm) was inserted so as to occupy a minimum space of 10 mm for casting of the stacking gel between the bottom of the sample well and the interface of the stacking gel with the resolving gel, for optimum stacking effect. Once assembled, the cassette was warmed to 65°-70° C. by placing it 6 to 8 inches (15.25-20.3 cm) beneath an infrared lamp.

Casting the Resolving Gel: The top clamps on either side of the cassette were removed. A microspatula was carefully inserted and twisted to widen slightly the cassette opening. The liquefied resolving gel solution was carefully introduced into the warmed cassette by gently squeezing the liquefied mixture from the bottle. Care was taken to avoid the production of air bubbles. The spatula was removed and the top clamps replaced. The gel was cooled for 30 minutes at room temperature. After cooling, large bottom clamps were placed on the top of the cassette and the cassette inverted 180°. The top side clamps were then removed and the stacking spacer was removed. The top side clamps were then replaced.

Casting the Stacking Gel: An agarose stacking gel, in 0.125M Tris buffer, pH 8.8, containing 0.006 mg/mL phenol red tracking dye (which travels with the leading ion front) was used. The liquefied stacking gel solution was carefully introduced into the stacking gel space in the cassette by gently squeezing the gel solution from the bottle. The production of air bubbles was avoided. Without delay, a comb was inserted 5 mm deep into the stacking gel. The stacking gel sat for 5 minutes at room temperature, and the entire cassette was then refrigerated at 4° C. for 30 minutes. After cooling, the gel was allowed to warm at room temperature for about 20 minutes, after which all the clamps were removed and the cassette was placed flat on the counter top. The comb was gently removed.

Preparing the Samples: Protein samples were suspended in a Tris-SDS-protein sample buffer composed of 0.06M Tris buffer HCl, pH 6.8; 2% SDS, 10% glycerol; 1% 2-mercaptoethanol; 0.025% phenol red; 0.25% bromophenol blue. Stock solutions of marker proteins are composed of 10 mg of each protein in 1 mL distilled water. A working solution was made by diluting 10 $\mu$L combined stock solution +100 $\mu$L sample buffer +280 $\mu$L distilled water, heating at 90° C. for 4 minutes and cooling and stored at room temperature. Ten (10) $\mu$L were applied per well. The total protein applied per well equalled 250 ng. The following proteins have been used as molecular weight markers (Daltons): myosin (212,000), $\beta$-galactosidase (116,000), phosphorylase b (92,500), bovine serum albumin (68,000), catalase (57,500), ovalbumin (43,000), carbonic anhydrase (29,000), soybean trypsin inhibitor (20,100), myoglobin (16,950), lysozyme (14,300), cytochrome C (11,700), and aprotinin (6500). A whole cell preparation of *E. coli* water soluble proteins also was prepared. A 100 mL volume of LB broth (a product of Difco) was made and inoculated with *E. coli* from a freshly prepared isolation plate. The broth culture was incubated 24 hours, then harvested by centrifugation, 5000 rpm for 15 minutes, the pellet was rinsed with distilled water, and resuspended and sonicated for 4×15 seconds in 10 mL's distilled water. Centrifuged at 5000 rpm for 15 minutes, the supernatant was aliquoted at 300 $\mu$L per vial, and frozen. To use, the aliquot was thawed and a 100 $\mu$L sample buffer (above) was added. The vials were then heated at 90° C. for four minutes. The vial contents were capable of storage for one week at room temperature.

Electrophoresis Procedure utilized: The cassette was clamped in a Studier-type vertical electrophoresis apparatus. Electrophoresis was effected in a Tris-borate electrode buffer [0.05M Tris, base; 0.09M boric acid, 0.1% SDS, pH 8.3] at 25 mA constant current for from 2 to 3 hours. The electrophoresis was completed when the phenol red tracking dye, included in the stacking gel, reached the bottom of the resolving gel. The reference tracking dye present in the sample buffer (bromophenol blue) was commonly used to calculate the relative mobility ($R_f$) of the sample proteins.

Staining and Drying: The proteins were fixed and stained with aqueous Coomassie staining solution (composed of 0.05% Coomassie brilliant blue R-250, in 40% methanol and 10% acetic acid) for 4 hours or overnight, at room temperature. They were then destained for 2 to 4 hours in 40% methanol, 10% acetic acid. They were then placed in a preservative bath, 5% glycerol, for one hour, and dried by clamping the gel to a glass plate, gel outward, and letting it air dry overnight.

The dried gel contained highly resolved protein patterns of both the protein standards and the *E. coli* proteins, thus indicating that the inventive gel compositions were effective for sieving lower molecular weight proteins.

EXAMPLE 3

Preparation of Inventive Agarose Blend Stacking Gel System

A. Small-pore resolving gel (irradiation depolymerization):

Component 1 was hydroxy-$C_{2-4}$-alkoxylated agarose powder (SeaPlaque ®, a product of FMC Corporation, BioProducts Group, Rockland, Me. 04841 U.S.A.).

Component 2 was a 1,2-dihydroxy-propyl agarose powder (glycerated agarose as described in U.S. Pat. No. 4,312,727, Example 1), which was then irradiation depolymerized. Depolymerization was effected by exposing the powder to gamma radiation at a 600 mR dosage, which resulted in the reduction of the viscosity of a 3% solution to 30–40 cps at 75° C.

Components 1 and 2 were blended in a 1:1 w/w ratio and 6 g of the blend were dissolved in 100 mL of a 0.5M Tris base buffer containing 0.4M boric acid, pH 8.5. The viscosity of the resulting blend solution at 75° C. was within 400–600 cps. The agarose blend had both low gelling (24°–28° C.) and low remelting (65°–70° C.) temperatures, enabling manageable gel casting and preparative procedures for protein recovery.

B. Large pore stacking gel

As a modification of the gel system combination of Example 1, 1.5% EDAC-agarose in 0.125M Tris-HCl buffer at pH 6.8 was used as the stacking gel. The discontinuity in pH improved the "stacking" of dilute protein samples. The increase of agarose percentage was effected in order to increase the gel strength and allow easier removal of the sample comb.; the stacking gel B was superposed adjacent the resolving gel A in similar manner to above Example 2. The resulting gel B was a stacking gel in that it allowed proteins introduced into it to concentrate into a narrow band before entering the small pore agarose resolving gel A. EDTA to a final concentration of 1 mM was added to the buffers of both the resolving gel and the stacking gel to serve as an inhibitor to the growth of microorganisms during storage. At this low concentration, the EDTA had no effect on the separation of proteins using the inventive gel system.

EXAMPLE 4

Preparation of Inventive Agarose Blend Stacking Gel System

A. Small-pore resolving gel (thermal depolymerization):

Component 1 was hydroxy-$C_{2-4}$-alkoxylated agarose powder (SeaPlaque ®, a product of FMC Corporation, Bioproducts Group, Rockland, Me. 04841, U.S.A.) which was thermally depolymerized by placing it in a sealed bottle and exposing it to dry heat at 100° C. for 52 hours. The depolymerization reduced the viscosity of a 3% solution to 5–15 cps at 75° C.

Component 2 was 1,2-dihydroxy-propyl agarose (glycerated agarose as described in U.S. Pat. No. 4,312,727 Example 1).

Components 1 and 2 were blended at a 1:1 w/w ratio and 6 g of the blend were dissolved in 100 ml of the buffer base used in part A of Example 3. The viscosity of the resulting solution was within 400-600 cps at 75° C. The agarose blend had both low gelling (24°-28° C.) and low remelting (65°-70° C.) temperatures, enabling manageable gel casting and preparative procedures for protein recovery. This small pore resolving gel per se comprises one embodiment of this invention and comprises another embodiment when utilized in combination with a large pore stacking gel.

B. Large pore stacking gel

In similar manner to above Example 3 part B, an EDAC-agarose stacking gel was prepared. A 1.5% solution was prepared by dissolving 1.5 g of this agarose derivative in 100 ml of 0.125M Tris-HCl buffer—pH 6.8. The resulting gel B was a stacking gel in that it allowed proteins introduced into it to concentrate into a narrow band before entering the small pore agarose resolving gel A. EDTA to a final concentration of 1 mM was added to the buffers of both the resolving gel and the stacking gel to serve as an inhibitor to the growth of microorganisms during storage. At this low concentration, the EDTA had no effect on the separation of proteins using the inventive gel system.

EXAMPLE 5

Comparison of Example Products

A comparison was made between the resolving gel products of Examples 1, 3, and 4, by comparing molecular weight (range $1 \times 10^{3-6}$) against relative mobility (range 0.0-1.0) for each product. Plotting 8 values for a composition containing irradiation depolymerized hydroxy-$C_{2-4}$-alkoxylated agarose as Component 1 [Example 1]; 10 values for a composition containing thermally depolymerized hydroxy-$C_{2-4}$-alkoxylated agarose as Component 1 [Example 4]; and 10 values for a composition containing irradiation depolymerized 1,2-dihydroxy-propyl agarose as Component 2 [Example 3]; the resulting curves were statistically the same. The overlapping of physical characteristics for the small-pore resolving gels of all examples were also noted.

Based upon the above analysis, it was concluded that the small pore resolving gel compositions of this invention were equally effective regardless the manner of the depolymerization of one component, and regardless which of the two components were depolymerized.

EXAMPLE 6

Elution of Protein from Inventive Resolving Gels

Bovine serum albumin (BSA) which was $^{14}$C labeled, was electrophoresed in a resolving gel composition prepared according to Example 1A. The gel sample was then cut out without prior fixing or staining of the gel, and then mixed with an aqueous solution containing 50 mM Tris-HCl, 1 mM EDTA, pH 8, in a 1:9 v/v ratio. It was then "freeze/squeezed" by known technique, as the result of which greater than 90% of the radioactive labeled BSA was recovered in the liquid supernatant. This was true as well for 100 μg of protein, and with or without the addition of 1M NaCl or 1% SDS to the dilution buffer.

In the "freeze/squeeze" method utilized, dilution of the gel composition was followed by freezing at −20° or −70° C., further followed by centrifugation at 13,000 G's for 10 to 20 minutes at 4° C. This yielded a liquid supernatant which contained a volume that followed the dilution of the gel composition in roughly a linear fashion. That is, for a 1:1 dilution (producing a 3% gel), roughly 50% of the volume was recovered as liquid following the freeze/squeeze. For a 1:9 dilution (producing a 0.6% gel), roughly 90% of the volume was recovered as liquid following the freeze/squeeze.

When the protein was fixed in the gel composition (with 45% methanol, 10% acetic acid), stained with Coomassie blue, and then destained, none of it would elute from the gel composition with this procedure. However, by adding SDS to the dilution buffer, up to 90% of the protein could be recovered. Finally, when unfixed proteins were recovered by the freeze/squeeze method, then concentrated by acetone precipitation, they electrophoresed similarly to unrecovered "normal" proteins. Proteins under 100 kD did especially well in this procedure.

EXAMPLE 7

Storage Stability of the Gel Composition

A five month study of the stability of the inventive resolving gel compositions according to Example 1A was conducted. The gel compositions were stored at temperatures of 4° C. and 23° C. (ambient). Little, if any, difference could be observed in the sieving properties of the two gel compositions, as compared with a similarly prepared fresh sample, after five months in storage, although storage at 4° C. appeared to be optimal.

EXAMPLES 8 through 12

Variations in the Resolving Gel Composition

Six (6) grams of each single component agarose resolving gel composition described below were dissolved in 100 mL of a buffer containing 0.5M Tris and 0.4M boric acid at pH 8.5. The viscosity of the resulting solution at 75° C. was within the range of 400-600 mPa's. The single component gels were used as the resolving gel component in the gel system described in Example 3. The resulting resolving gels had both low gelling (24°-28° C.) and remelting (65°-70° C.) temperatures, except that the resolving gel of example 9 had a melting temperature of about 85°-90° C. and a gelling temperature of about 35°-40° C. The resolving gels of Examples 9, 11, and 12 were within the scope of this invention in that they enabled manageable gel casting and therefore facilitated preparative procedures for protein recovery.

EXAMPLE 8—(Comparison)

Preparation of a resolving Gel Composition (single depolymerized native agarose)

A one component resolving gel was prepared by exposing low electroendosmosis agarose powder (Sea-Kem ® LE a product of FMC Corporation, BioProducts Group, Rockland, Me. 04841 U.S.A.) to gamma irradiation of 600 mR. This treatment reduced the viscosity of a 3% solution to 30-40 mPa's at 75° C. This resolving gel was outside the scope of this invention because it did not contain at least one derivatized polysaccharide component, and was distinctly less sieving than resolving gels within the scope of this invention.

EXAMPLE 9

Preparation of a Resolving Gel Composition (single agarose derivatized before depolymerization)

A one component resolving gel was prepared by exposing 1,2-dihydroxy-propyl agarose powder (glycerated agarose, described in Example 1 of previously cited U.S. Pat. No. 4,312,727), to gamma irradiation of 600 mR. This treatment reduced the viscosity of a 3% solution to 30–40 mPa's at 75° C.

EXAMPLE 10—(Comparison)

Preparation of a Resolving Gel Composition (single agarose derivatized before depolymerization)

A one component resolving gel was prepared by exposing hydroxy-$C_{2-4}$-alkoxylated agarose powder (SeaPlaque® a product of FMC Corporation, BioProducts Group, Rockland, Me., 04841 U.S.A.) to gamma irradiation of 600 mR. This treatment reduced the viscosity of a 3% solution to 30–40 mPa's at 75° C. Although Example 10 is outside the scope of this invention, Examples 9 and 10 taken together demonstrate the independence of viscosity control (achieved by depolymerization) and sieving control (achieved by derivatization).

EXAMPLE 11

Preparation of a Resolving Gel Composition (single agarose derivatized after depolymerization)

A one component resolving gel was prepared by exposing low electroendosmosis agarose powder (SeaKem® LE a product of FMC Corporation, BioProducts Group, Rockland, Me. 04841, U.S.A.) to gamma irradiation of 600 mR, which treatment reduced the viscosity of a 3% solution to 30–40 mPa's at 75° C., followed by the addition of 1,2-dihydroxy-propyl moieties.

EXAMPLE 12

Preparation of a Resolving Gel Composition (single agarose derivatized after depolymerization)

A one component resolving gel was prepared by exposing low electroendosmosis agarose powder (SeaKem® LE a product of FMC Corporation, BioProducts Group, Rockland, Me. 04841, U.S.A.) to gamma irradiation of 600 mR (this treatment reduces the viscosity of a solution to 30–40 mPa's at 75° C.) followed by the addition of hydroxy-$C_{2-4}$-alkoxylate moieties.

EXAMPLE 13

Preparation of a Resolving Gel Composition (depolymerized native agarose+derivatized agarose)

Component 1 was prepared by exposing low electroendosmosis native (underivatized) agarose powder (SeaKem® LE a product of FMC Corporation, BioProducts Group, Rockland, Me. 04841 U.S.A.) to gamma irradiation of 600 mR. This treatment reduced the viscosity of a 3% solution to 30–40 mPa's at 75° C.

Component 2 was 1,2-dihydroxy-propyl agarose (glycerated agarose, described in Example 1 of previously cited U.S. Pat. No. 4,312,727).

Both components were blended in a 1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

EXAMPLE 14

Preparation of a Resolving Gel Composition (depolymerized native agarose+derivatized agarose)

Component 1 was prepared by exposing low electroendosmosis native (underivatized) agarose powder (SeaKem® LE a product of FMC Corporation, BioProducts Group, Rockland, Me. 04841 U.S.A.) to gamma irradiation of 600 mR. This treatment reduced the viscosity of a 3% solution to 30–40 mPa's at 75° C.

Component 2 was hydroxy-$C_{2-4}$-alkoxylated agarose powder (SeaPlaque® a product of FMC Corporation, BioProducts Group, Rockland, Me. 04841, U.S.A.).

Both components were blended in 1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

EXAMPLE 15

Preparation of a Resolving Gel Composition (agarose derivatized after depolymerization)

Component 1 was prepared by exposing low electroendosmosis native (underivatized) agarose powder (SeaKem® LE a product of FMC Corporation, BioProducts Group, Rockland, Me. 04841 U.S.A.) powder to gamma irradiation of 600 mR (this treatment reduces the viscosity of a 3% solution to 30–40 mPa's at 75° C.), followed by the addition of 1,2-dihydroxy-propyl moieties.

Component 2 was hydroxy-$C_{2-4}$-alkoxylated agarose powder (SeaPlaque®, a product of FMC Corporation, BioProducts Group, Rockland, Me. 04841 U.S.A.).

Both components were blended in a 1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

EXAMPLE 16

Preparation of a Resolving Gel Composition (derivatization after depolymerization)

Component 1 was prepared by exposing low electroendosmosis native (underivatized) agarose powder (SeaKem® LE, a product of FMC Corporation, Rockland, Me. 04841, U.S.A.) to gamma irradiation of 600 mR (this treatment reduced the viscosity of a 3% solution to 30–40 mPa's at 75 ° C.), followed by the addition of hydroxyethyl moieties.

Component 2 was 1,2-dihydroxy-propyl agarose (glycerated agarose, described in Example 1 of previously cited U.S. Pat. No. 4,312,727).

Both components were blended in a 1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

EXAMPLE 17

Preparation of a Resolving Gel Composition (all components depolymerized)

Component 1 was prepared by exposing 1,2-dihydroxypropyl agarose powder (glycerated agarose, described in Example 1 of previously cited U.S. Pat. No. 4,312,727) to gamma irradiation of 600 mR. This treatment reduced the viscosity of a 3% solution to 30–40 mPa's at 75° C.

Component 2 was prepared by exposing hydroxy-$C_{2-4}$-alkoxyl agarose powder (SeaPlaque ®, a product of FMC Corporation, BioProducts Group, Rockland, Me. 04841, U.S.A.) to gamma irradiation of 600 mR. This treatment reduced the viscosity of a 3% solution to 30–40 mPa's at 75° C.

Both components were blended at a 1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

EXAMPLE 18

Preparation of a Resolving Gel Composition (three components, one depolymerized)

Component 1 was prepared by exposing hydroxy-$C_{2-4}$-alkoxylated agarose powder (SeaPlaque ®, a product of FMC Corporation, Bioproducts Group, Rockland, Me. 04841, U.S.A.) to gamma irradiation of 600 mR. This treatment reduced the viscosity of a 3% solution to 30–40 mPa's at 75° C.

Component 2 was 1,2-dihydroxy-propyl agarose (glycerated agarose, described in Example 1 of previously cited U.S. Pat. No. 4,312,727).

Component 3 was carboxymethyl agarose which was prepared by reacting agarose with monochloroacetic acid in the presence of sodium hydroxide, as described in Example 2 of U.S. Pat. No. 3,507,851.

All three components were blended in a 1:1:1 (w/w) ratio and six (6) grams were dissolved in 100 mL of a buffer containing 0.5M Tris and 0.4M boric acid at pH 8.5. The viscosity of the resulting solution at 75° C. was within the range of 400–600 mPa's. In addition the resulting agarose blend had both low gelling (24°–28° C.) and remelting (65°–70° C.) temperatures enabling manageable gel casting and preparative procedures for protein recovery.

We claim:

1. An aqueous electrophoretic resolving gel composition comprising:
   (A) two hydrogels, at least one of which has been derivatized and, independently, at least one of which has been depolymerized sufficiently to reduce the casting-effective viscosity of the total resolving gel composition; other than a combination of (i) hydroxyethyl agarose which was subsequently depolymerized and (ii) 1,2-dihydroxypropyl agarose;
   (B) water; and
   (C) a resolving gel buffer.

2. An electrophoretic discontinuous stacking gel system comprising:
   (I) a resolving gel composition comprising;
      (A) one or more thermo- and/or pH- reversible hydrogels, at least one of which has been derivatized and, independently, at least one of which has been depolymerized sufficiently to reduce the casting-effective viscosity of said resolving gel composition;
      (B) water;
      (C) a resolving gel buffer; and
      (D) optionally, about 1–5 % w/w of said resolving gel, of at least one low molecular weight polyol; in electrophoretic-gel-operative combination with:
   (II) a superposed or adjacent stacking gel which is discontinuous from said resolving gel as to at least one of: pore size, ionic strength, ionic composition, or pH, comprising:
      (A) one or more derivatized or native thermo- and/or pH- reversible hydrogels;
      (B) water; and
      (C) a stacking gel buffer.

3. The compositions of any one of preceding claims 1, or 2 wherein each said hydrogel is a polysaccharide.

4. The compositions of any one of preceding claims 1, or 2 wherein each said hydrogel is agar, agarose, alginate, carrageenan, curdlan, gellan, Konjac, pectin, pullulan, or a hydrogel formed by the combination thereof with either another polysaccharide or a non-polysaccharide polymer which associates firmly with the gel-forming polymers so that it does not significantly dissociate under electrophoretic conditions.

5. The compositions of any one of preceding claims 1, or 2 wherein each said hydrogel is an agarose.

6. The compositions of any one of preceding claims 1, or 2 wherein at least two said hydrogels are present in said resolving gel.

7. The compositions of any one of preceding claims 1, or 2 wherein said resolving gel hydrogels are one or more of:
   (a) hydroxyalkoxylated agarose,
   (b) dihydroxyalkyl agarose, or
   (c) native agarose
in which where a derivatized agarose, it has been depolymerized either before or after its derivatization.

8. The compositions of any one of preceding claims 1, or 2 wherein said resolving gel hydrogels are a mixture of
   (a) hydroxy-$C_{2-4}$-alkoxylated agarose, and
   (b) 1,2-dihydroxypropyl agarose, at least one of which has been depolymerized before its derivatization.

9. The compositions of claim 7 wherein the weight ratio a:b is 1:.11–9.

10. The composition of claim 9 wherein the weight ratio a:b is about 1:1.

11. The compositions of any one of preceding claims 1, or 2 wherein said resolving gel hydrogels are a mixture of
   (a) hydroxy-$C_{2-4}$-alkoxylated agarose, and (b) 1,2-dihydroxypropyl agarose, at least one of which has been depolymerized after its derivatization.

12. The compositions of any one of preceding claims 1, or 2 wherein hydroxyethyl agarose is the depolymerized hydrogel.

13. The compositions of any one of preceding claims 1, or 2 wherein 1,2-dihydroxypropyl agarose is the depolymerized hydrogel.

14. The compositions of any one of preceding claims 1, or 2 wherein said resolving gel viscosity is reduced to about 5-40 cps when measured at 75° C. in a 3% aqueous solution.

15. The composition of claim 14 wherein said viscosity reduction is effected by at least one of: acid hydrolysis; alkaline hydrolysis; catalytic hydrolysis; enzyme hydrolysis; exposure to gamma radiation; exposure to radiation other than gamma; mechanical shearing; or thermal depolymerization.

16. The composition of claim 14 wherein said viscosity reduction is effected by at least one of: acid hydrolysis; exposure to gamma radiation; or thermal depolymerization.

17. The composition of claim 14 wherein said viscosity is reduced by exposure to gamma radiation.

18. The composition of claim 14 wherein said viscosity is reduced by thermal degradation.

19. The composition of claims 1, or 2 wherein the total hydrogel content of the resolving gel is about 2-12% w/v of the resolving gel.

20. The composition of claims 1, or 2 wherein the total hydrogel content of the resolving gel is about 4-8% w/v of the resolving gel.

21. The composition of claims 1, or 2 wherein said resolving gel buffer comprises at least one of HEPES, glycine, Tris, triethanolamine, or triethylamine.

22. The composition of claims 1, or 2 wherein said resolving gel buffer comprises a borate compound or complex.

23. The composition of claims 1, or 2 wherein said resolving gel buffer is Tris-borate, said stacking gel buffer when present is Tris-glycine, and said electrode buffer when present is Tris-HCl.

24. The composition of claim 2 wherein the discontinuity is at least partially based upon pores of said resolving gel being smaller than pores of said stacking gel.

25. The composition of claim 2 wherein said discontinuity is at least partially based upon a differential between said resolving gel composition and said stacking gel composition as to at least one of: ionic strength, ionic composition, or pH.

26. The composition of claim 2 wherein said stacking gel comprises an agarose or derivatized agarose having a high gel strength and a low (EEO) value.

27. The composition of claim 25 wherein said EEO value has an electroendomosis value, $(M_n)$ of from $(-)$ 0.15 to $(+)$ 0.05.

28. The composition of claim 25 wherein said EEO value has an electroendomosis value, $(m_r)$ of from $(-)$ 0.10 to $(+)$ 0.05.

29. The composition of claim 25 wherein said EEO value has an electroendomosis value, $(m_r)$ of from $(-)$ 0.03 to $(+)$ 0.03.

30. The composition of claim 25 wherein said EEO value has an electroendomosis value, $(m_r)$ approaching zero.

31. The composition of claim 2 wherein said discontinuous stacking gel is EDAC-agarose or 1-ethyl-3(3-dimethylaminopropyl)carbodiimide hydrochloride-treated ion-exchanged agarose (EDAC-agarose) or dimethylaminoethyl-agarose (DEAE-agarose).

32. The composition of claim 2 wherein said polyol is present in about 1-5 % wt of the resolving gel composition.

33. The composition of claim 2 wherein said polyol is present and is: ethylene glycol, glycerol, sucrose, sorbitol, a polyoxyethylene glycol of 200-600D, or a mixture thereof.

* * * * *